(12) United States Patent
Baek et al.

(10) Patent No.: US 11,213,663 B2
(45) Date of Patent: Jan. 4, 2022

(54) MICRONEEDLE AND METHOD OF MANUFACTURING THE SAME

(71) Applicant: QuadMedicine, Seongnam-si (KR)

(72) Inventors: Seung Ki Baek, Seoul (KR); Myun Hwan Ahn, Namyangju-si (KR)

(73) Assignee: QuadMedicine, Seongnam-si (KR)

( * ) Notice: Subject to any disclaimer, the term of this patent is extended or adjusted under 35 U.S.C. 154(b) by 0 days.

(21) Appl. No.: 15/864,043

(22) Filed: Jan. 8, 2018

(65) Prior Publication Data

US 2018/0243543 A1 Aug. 30, 2018

(30) Foreign Application Priority Data

Feb. 27, 2017 (KR) ........................ 10-2017-0025715

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61M 2037/0023* (2013.01); *A61M 2037/0046* (2013.01); *A61M 2037/0053* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 2002/0082543 A1* | 6/2002 | Park | ..................... | A61B 5/1411 604/21 |
| 2003/0175355 A1* | 9/2003 | Tobyn | .................... | A61J 7/0061 424/489 |
| 2006/0051404 A1* | 3/2006 | Yeshurun | ............. | A61B 17/205 424/449 |
| 2010/0228203 A1* | 9/2010 | Quan | ................ | A61M 37/0015 604/272 |
| 2011/0014060 A1* | 1/2011 | Bolcavage | .............. | F01D 5/288 416/241 R |
| 2012/0265145 A1* | 10/2012 | Mefti | ................ | A61M 37/0015 604/173 |
| 2014/0005606 A1* | 1/2014 | Chen | ..................... | A61K 9/0021 604/173 |
| 2014/0128811 A1 | 5/2014 | Ferguson et al. | | |
| 2015/0290163 A1 | 10/2015 | Quan et al. | | |
| 2015/0374620 A1* | 12/2015 | Sugahara | ............... | A61K 47/12 604/46 |
| 2016/0158512 A1* | 6/2016 | Tamaru | ............. | A61M 37/0015 604/173 |
| 2018/0064920 A1* | 3/2018 | Desimone | .............. | B33Y 80/00 |

FOREIGN PATENT DOCUMENTS

| | | |
|---|---|---|
| EP | 3 028 735 A1 | 6/2016 |
| JP | 2010-233674 A | 10/2010 |
| JP | 2011-206178 A | 10/2011 |
| JP | 2013-248299 A | 12/2013 |
| JP | 2015-205094 A | 11/2015 |
| JP | 2015-217043 A | 12/2015 |
| JP | 2016-30072 A | 3/2016 |
| JP | 5879927 B2 | 3/2016 |
| JP | 2016-106757 A | 6/2016 |
| JP | 2017-19785 A | 1/2017 |
| KR | 10-2003-0077473 A | 10/2003 |
| KR | 10-2014-0084042 A | 7/2014 |
| KR | 10-2015-0082234 A | 7/2015 |
| KR | 10-2016-0058261 A | 5/2016 |
| WO | 2008/130587 A2 | 10/2008 |
| WO | 2012-144718 A1 | 10/2012 |
| WO | 2014-069615 A1 | 5/2014 |
| WO | WO-2015016235 A1 * | 2/2015 ........ A61M 37/0015 |

OTHER PUBLICATIONS

Canetti et al. Journal of Polymer Science Part B:Polymer Physics 2014 52:1168-1177), (Year: 2014).*
Farndon Nitrogen. Tarrytown:Marshall Cavendish Corporation 1999, p. 6 (Year: 1999).*
Safety Data Sheet for alginic acid p. 1-6 (Year: 2014).*
Safety Data Sheet for sucrose p. 1-7 (Year: 2014).*
Safety Data Sheet for sodium polyacrylate p. 1-7 (Year: 2015).*
Safety Data Sheet for sodium dodecyl sulfate p. 1-2 (Year: 2008).*
Langevin et al. Journal of Applied Physiology 2001 91:2471-2478 (Year: 2001).*
Yang et al. Nature Communications 2013 4:1702, pp. 1-10 (Year: 2013).*
Chen et al. Biomaterials 2013 34:3077-3086 (Year: 2013).*
www3.ipc.org.es/guia_colocacion/info_tec_colocacion/mat_agarre/adherencia/medida.html 3 pages (Year: 2007).*
Notice of Office Preliminary Rejection of Korean Patent Application 10-2017-0025715, dated Apr. 20, 2017.
Leonard Y. Chu et al., "Separable Arrowhead Microneedles", Feb. 10, 2011, p. 242-249, vol. 149(3), J Control Release, NIH Public Access Author Manuscript.
Communication dated Jun. 29, 2018, issued by the British Patent Office in counterpart British Patent Application No. 1800858.1.
Communication dated Jun. 12, 2018, issued by the Japanese Patent Office in counterpart Japanese Patent Application No. 2018-002588.
Communication dated Mar. 6, 2018, issued by the Japanese Patent Office in counterpart Japanese Application No. 2018-002588.
Communication dated May 20, 2019, issued by the British Patent Office in counterpart British Application No. 1800858.1.

* cited by examiner

*Primary Examiner* — Robert A Wax
*Assistant Examiner* — Caralynne E Helm
(74) *Attorney, Agent, or Firm* — Sughrue Mion, PLLC (57) ABSTRACT

Disclosed is a microneedle including at least one tip portion that is capable of penetrating the skin and includes a liquid medicine melted in the skin; a base portion supporting the at least one tip portion; and at least one guide portion that is provided between the at least one tip portion and the base portion, is made of a non-soluble material, and is protruded in a direction in which the at least one tip portion penetrates the skin to couple with the at least one tip portion. In accordance with such a configuration, the at least one tip portion may be instantly separated in a short time, whereby superior liquid medicine supplyability is exhibited.

3 Claims, 8 Drawing Sheets

FIG.7

MICRONEEDLE AND METHOD OF MANUFACTURING THE SAME

CROSS-REFERENCE TO RELATED APPLICATION

This application claims the priority benefit of Korean Patent Application No. 10-2017-0025715, filed on Feb. 27, 2017 in the Korean Intellectual Property Office, the disclosure of which is incorporated herein by reference.

BACKGROUND OF THE DISCLOSURE

Field of the Disclosure

The present disclosure relates to a microneedle and a method of manufacturing the same, more particularly to a microneedle capable of supplying a predetermined amount of liquid medicine by instantly separating a tip portion penetrating the skin in a short time and a method of manufacturing the same.

Description of the Related Art

Various drug delivery technologies, such as oral delivery, injection, transdermal delivery, and mucosal delivery, have been used. Thereamong, transdermal drug delivery technology, which is a technology of delivering drugs through the skin using patches, creams, etc., has advantages in that it is not affected by intestinal metabolism and continuous drug delivery may be accomplished by using patches.

As general transdermal drug delivery methods, there are a passive transdermal drug delivery system and an active transdermal drug delivery system. A passive transdermal drug delivery system, which is a passive method depending upon physicochemical properties of a drug, is characterized by spreading a cream, a patch, an ointment, etc. on the skin. Meanwhile, such a passive transdermal drug delivery method has a limitation in that the molecular weight of a drug capable of being delivered through the skin is 500 Da or less.

In addition, in the case of an active transdermal drug delivery method, an effective ingredient is delivered by physically penetrating the stratum corneum, which has a thickness of 10 µm, with a microneedle so as to overcome limitation in penetrating the skin. In such active transdermal drug delivery, a solid cream-type microneedle, a microneedle coated with an effective ingredient, a microneedle that melts in water, a hollow microneedle smaller than conventional needles, and the like are used.

Meanwhile, the solid cream-type microneedle and the water-melted microneedle have problems, such as inaccurate dose delivery, reduction of drug stability due to long production time, drug loss in a drying process, and delayed penetration time, in delivering an effective ingredient into the skin. Accordingly, various research into increasing effective ingredient transference ability of a microneedle into the skin has been continuously conducted in recent years.

RELATED DOCUMENTS

Patent Documents (Patent Document 1) Japanese Patent No. 5879927
(Patent Document 2) US Patent Application Publication No. 2014-0128811

SUMMARY OF THE DISCLOSURE

Therefore, the present invention has been made in view of the above problems, and it is one object of the present invention to provide a microneedle capable of effectively delivering a predetermined amount of liquid medicine in a short time.

It is another object of the present invention to provide a method of manufacturing a microneedle, a manufacturing time of which is reduced and thus which is capable of penetrating a predetermined amount of liquid medicine into the skin without loss of a liquid medicine.

In accordance with an aspect of the present invention, the above and other objects can be accomplished by the provision of a microneedle including at least one tip portion that is capable of penetrating the skin and includes a liquid medicine melted in the skin; a base portion supporting the at least one tip portion; and at least one guide portion that is provided between the at least one tip portion and the base portion, is made of a non-soluble material, and is protruded in a direction in which the at least one tip portion penetrates the skin to couple with the at least one tip portion.

In accordance with an aspect, the at least one guide portion may be integrally formed with the base portion, and the at least one guide portion may be coupled to the at least one tip portion with a coupling force smaller than a force with which the skin holds the at least one tip portion.

In accordance with an aspect, a distal end of the at least one tip portion may have a pointed shape in the penetration direction, and a lower end of the at least one tip portion may be respectively coupled with the at least one guide portion.

In accordance with an aspect, the at least one guide portion may include a support member extending toward the at least one tip portion from the base portion; and at least one guide protrusion protruding toward the at least one tip portion from the support member.

In accordance with an aspect, the at least one guide protrusion may extend and protrude from at least one side of the support member.

In accordance with an aspect, the at least one guide protrusion may protrude from an upper surface of the support member toward the at least one tip portion.

In accordance with an aspect, the support member and the at least one guide protrusion may be formed as one body.

In accordance with an aspect, a concave semicircular support groove may be formed on an upper surface of the support member, and the at least one guide protrusion may extend from a rim of the support groove.

In accordance with an aspect, the at least one guide protrusion may protrude along a rim of the support member to have a donut-shape cross section.

In accordance with another aspect of the present invention, there is provided a method of manufacturing a microneedle, the method including forming at least one tip portion that is capable of penetrating the skin and includes a liquid medicine melted in the skin; and coupling at least one guide portion to the at least one tip portion such that the at least one guide portion respectively corresponds to the at least one tip portion.

In accordance with an aspect, the forming of the at least one tip portion may include preparing a mold having at least one tip groove; supplying a liquid medicine including at least a portion of a raw material or biodegradable polymer ingredient to the mold; and pressing the liquid medicine into the at least one tip groove to mold the at least one tip portion.

In accordance with an aspect, the mold may be a polydimethylsiloxane (PDMS) a mold and may include at least any one of polyurethane, a metal, a biocompatible aluminum material, a water-soluble polymer, a lipophilic polymer, and an amphiphilic, wherein the lipophilic polymer and the amphiphilic polymer include at least one of hydroxypropyl cellulose (HPC), hydroxypropyl methyl cellulose (HPMC), polycaprolactone (PCL), polyglycolide (PGA), polylactic acid (PLA), a polylactide-glycolide (PLGA) copolymer, polyvinylpyrrolidone (PVP), polyethylene glycol (PEG), polyethylene oxide (PEO), polypropylene oxide (PPO), poly (vinyl methyl ether) (PVME), poly(methyl acrylate) (PMA), propylene glycol, polyesteramide, polybutyric acid, acrylamide (acrylic amide), acrylic acid, hyaluronic acid (HA), and gelatin.

In accordance with an aspect, the liquid medicine may be made of a biocompatible material and an additive.

In accordance with an aspect, the biocompatible material may include at least any one of carboxymethyl cellulose (CMC), hyaluronic acid (HA), alginic acid, pectin, carrageenan, chondroitin sulfate, dextran sulfate, chitosan, polylysine, carboxymethyl chitin, fibrin, agarose, pullulan, polyanhydride, polyorthoester, polyetherester, polyesteramide, polybutyric acid, poly(valeric acid), polyacrylate, an ethylene-vinyl acetate polymer, acryl-substituted cellulose acetate, polyvinyl chloride, polyvinyl fluoride, polyvinyl imidazole, chlorosulphonate polyolefins, polyethylene oxide, polyvinylpyrrolidone (PVP), hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or at least any one of a copolymer of monomers forming this polymer and cellulose.

In accordance with an aspect, the additive may include at least any one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, gentiobiose, cetrimide (alkyltrimethylammonium bromide), cetrimonium bromide (hexadecyltrimethylammonium bromide (CTAB)), gentian violet, benzethonium chloride, docusate sodium salt, a SPAN-type surfactant, polysorbate (Tween)), sodium lauryl sulfate (sodium dodecyl sulfate (SDS)), benzalkonium chloride, and glyceryl oleate.

In accordance with an aspect, the method may include, after rapidly cooling the at least one tip portion, surface-coating the at least one tip portion with the liquid medicine.

In accordance with an aspect, in the rapid cooling, a refrigerant for inducing endothermic reaction including at least any one of liquid nitrogen at −196° C., tetrafluoroethane at −50° C., a Peltier element cooling fan −20° C., dry ice at −78° C., and a refrigerant including at least any one of carbon tetrachloride, trichlorofluoromethane, dichlorodifluoromethane, bromochlorodifluoromethane, dibromodifluoromethane, chlorotrifluoromethane, bromotrifluoromethane, tetrafluoromethane, chloroform, dichlorofluoromethane, chlorodifluoromethane, bromodifluoromethane, trifluoromethane, dichloromethane, chlorofluoromethane, methylene fluoride (difluoromethane), methyl chloride (chloromethane), methyl fluoride (fluoromethane), methane, hexachloroethane, pentachlorofluoroethane, tetrachlorodifluoroethane, trichlorotrifluoroethane, dichlorotetrafluoroethane (1,2-dichlorotetrafluoroethane), dibromotetrafluoroethane, chloropentafluoroethane, hexafluoroethane, pentachloroethane, dichlorotrifluoroethane (2,2-dichloro-1, 1,1-trifluoroethane), chlorotetrafluoroethane, pentafluoroethane, tetratrifluoroethane, tetrafluoroethane, trichloroethane (methyl chloroform), dichlorofluoroethane (1,1-dichloro-1-fluoroethane), chlorodifluoroethane, trifluoroethane, dichloroethane, difluoroethane, ethyl chloride (chloroethane), ethane, dichlorohexafluoropropane, liquid helium, and liquid oxygen may be used.

In accordance with an aspect, the surface-coating may be performed by spraying a coating agent including the liquid medicine to the at least one tip portion or immersing the at least one tip portion in the coating agent under vacuum or in a dry air environment having humidity of less than 50%.

In accordance with an aspect, the coating agent may be mixed in a ratio of 0.1% to 30% of an effective ingredient with water.

In accordance with an aspect, the coating agent may include a thickener, wherein the thickener includes any one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly(butyric acid), poly(valeric acid), polyacrylate, an ethylene-vinyl acetate polymer, acryl-substituted cellulose acetate, polyvinyl chloride, polyvinyl fluoride, poly(vinyl imidazole), chlorosulphonate polyolefins, polyethylene oxide, polyvinylpyrrolidone (PVP), hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or at least one of a copolymer of monomers forming this polymer and cellulose.

In accordance with an aspect, the effective ingredient may include at least any one of α-interferon, β-interferon for multiple sclerosis, erythropoietin, follitropin β, follitropin α, G-CSF, GM-CSF, human chorionic gonadotropin, luteinizing hormone, salmon calcitonin, glucagon, a GNRH antagonist, insulin, human growth hormone, filgrastim, heparin, low-molecular-weight heparin, and somatotropin; or a vaccine including at least any one of Japanese encephalitis vaccine, rotavirus vaccine, influenza vaccine, polio vaccine, varicella vaccine, Alzheimer's disease vaccine, arteriosclerosis vaccine, cancer vaccine, nicotine vaccine, diphtheria vaccine, cervical cancer vaccine, meningococcal vaccine, tetanus vaccine, pertussis vaccine, Lyme disease vaccine, rabies vaccine, pneumococcal vaccine, yellow fever vaccine, cholera vaccine, vaccine exanthem, tuberculosis vaccine, rubella vaccine, measles vaccine, mumps vaccine, botulism vaccine, herpes virus vaccine, other DNA vaccines, hepatitis B vaccine, hyaluronic acid, Coenzyme Q10, chitosan, Botox, vitamins and vitamin derivatives, hydroxy acid, tetracycline, oxytetracycline, doxycycline, minocycline, benzocaine, mepivacaine, lidocaine, prilocaine, bupivacaine, etidocaine, articaine, procaine, propoxycaine, tetracaine, ropivacaine, butacaine, piperocaine, cocaine, chloroprocaine, proparacaine, and dyclonine.

In accordance with an aspect, the coating agent may include a water-soluble substance, the water-soluble substance including at least any one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

In accordance with an aspect, the method may include evaporating a solvent from the coated microneedle and waterproof-coating such that a coated surface is not affected by a solution, wherein, in the waterproof-coating, a solvent of a coated at least one tip portion is removed by at least any one of ultrasonic spray coating, atomization coating, electrospinning coating, and dip coating.

In accordance with an aspect, in the waterproof-coating, an end or the entire surface of the microneedle 1 may be waterproof-coated with a water-repellent agent including a mineral-based material or a lipid-based material, wherein the water-repellent agent includes at least any one of beeswax, oleic acid, soy fatty acid, castor oil, phosphatidylcholine, vitamin E (d-α-tocopherol/Vitamin E), corn oil mono-di-tridiglycerides, cottonseed oil, olive oil, peanut oil, peppermint oil, safflower oil, sesame oil, soybean oil, hydrogenated vegetable oils, hydrogenated soybean oil, capric triglycerides (caprylic/capric triglycerides derived from coconut oil or palm seed oil) and phosphatidylcholine, or is formed of a mixture thereof.

In accordance with an aspect, the coupling may include removing the liquid medicine molded outside the at least one tip groove of the mold; coupling the at least one guide portion to the at least one tip portion molded in the at least one tip groove; and removing the mold in a state wherein the at least one tip portion is coupled with at least one guide portion.

In accordance with an aspect, the at least one guide portion may be supported by a base portion, wherein the base portion includes at least any one of polyethylene (PE), polypropylene (PP), polytetrafluoroethylene (PTFE), polymethyl methacrylate (PMMA), ethylene vinyl acetate (EVA), polycaprolactone (PCL), polyurethane (PU), polyethylene terephthalate (PET), polyethylene glycol (PEG), polyvinyl alcohol (PVA), polylactide (PLA), a polylactide-glycolide (PLGA) copolymer, and polyglycolide (PGA).

In accordance with an aspect, the base portion and the at least one guide portion may be formed of an identical material.

In accordance with an aspect, a coupling force between the at least one tip portion and the at least one guide portion may be smaller than a force with which the skin holds the tip portion.

In accordance with an aspect, between the forming and the coupling, drying the at least one tip portion may be included.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Hereinafter, a preferred embodiment of the present disclosure is described with reference to the accompanying drawings.

Figure 1:
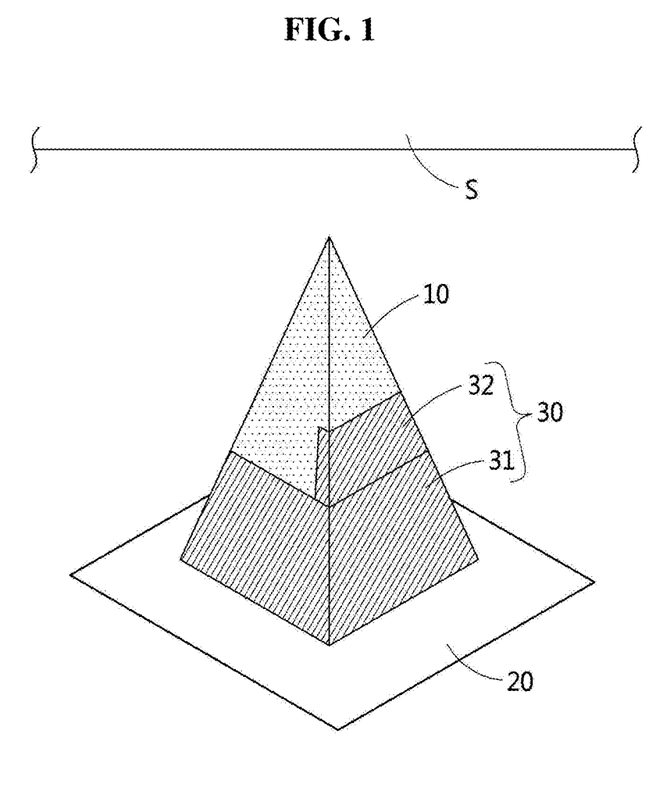
FIG. 1 is a perspective view schematically illustrating a microneedle according to a preferred embodiment of the present disclosure.
Figure 2:
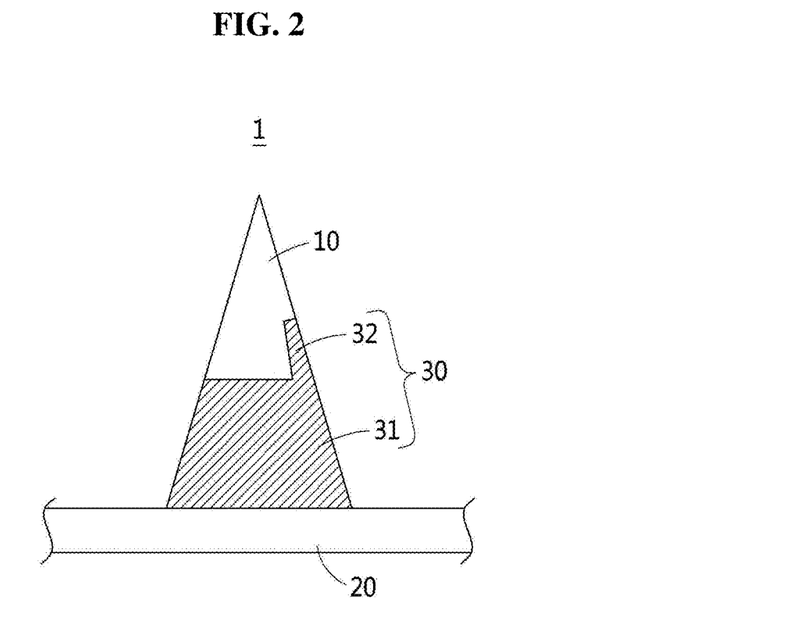
FIG. 2 schematically illustrates a side view of the microneedle illustrated in FIG. 1.

As illustrated in FIGS. 1 and 2, a microneedle 1 according to a preferred embodiment of the present disclosure includes a tip portion 10, a base portion 20, and a guide portion 30.

A plurality of tip portions 10, which is capable of penetrating the skin (S) and melted therein and include a liquid medicine, is prepared. A distal end of each of the tip portions 10 has a pointed tip shape with respect to a penetration direction into the skin (S). More particularly, the tip portion 10 has a cone or polygonal cone shape and may penetrate the skin (S). The tip portion 10 is formed of a liquid medicine, as a water-soluble polymer, which is capable of penetrating the skin (S) and being melted therein. A particular configuration of the tip portion 10 is described with reference to a manufacturing method thereof below.

The base portion 20 supports the plurality of tip portions 10. The base portion 20 does not include a liquid medicine, and may be separated after the tip portion 10 penetrates the skin (S). The base portion 20 is prepared in a kind of patch shape, thereby closely contacting the skin (S).

A plurality of guide portions 30, which is protruded in a direction in which the tip portions 10 penetrate the skin (S), is prepared such that each of the guide portions 30 is coupled to each of the tip portions 10. The guide portion 30 is provided between the base portion 20 and the tip portion 10 so that the guide portion 30 is coupled with a lower end of the tip portion 10 instead a pointed distal end of thereof. That is, the guide portion 30 extends toward the tip portion 10 from the base portion 20.

More particularly, the guide portion 30 includes a support member 31 extending toward the tip portion 10 from the base portion 20; and at least one guide protrusion 32 protruding toward the tip portion 10 from the support member 31.

The support member 31 is a kind of support end. Preferably, the support member 31 integrally extends from the base portion 20. In addition, with regard to the at least one guide protrusion 32 protruding toward the tip portion 10 from the support member 31, FIGS. 1 and 2 illustrate a guide protrusion protruding and extending from at least one surface of the support member 31 as an embodiment.

The guide protrusion 32 guides penetration of the tip portion 10 while supporting the tip portion 10 extending in a penetration direction. Here, the guide protrusion 32 integrally extends from the support member 31 extending from the base portion 20.

Meanwhile, the base portion 20 and the guide portion 30 are preferably made of a non-soluble material unlike the tip portion 10 penetrating the skin (S). Accordingly, the base portion 20 and the guide portion 30 do not interfere penetration force of the tip portion 10 and guide supply of a predetermined amount of liquid medicine into the skin (S).

In addition, the guide portion 30 is coupled with the tip portion 10 such that the guide portion may be instantly separated from the tip portion 10 penetrating the skin (S). More particularly, the guide portion 30 may guide separation of the tip portion 10 through coupling force between the guide portion 30 and the tip portion 10 based on a geometrical structure of the guide portion 30 protruding from the base portion 20.

That is, coupling force between the tip portion 10 and the guide portion 30 is about 0.0001 N to 1 N. The sum of elastic force, frictional force, and adhesive force of the skin (S), by which the tip portion 10 is held, is 1 N to 5 N. Accordingly, since the force of the skin (S) holding the tip portion 10 is larger than the coupling force between the tip portion 10 and the guide portion 30, the tip portion 10 penetrating the skin (S) may be instantly separated from the guide portion 30.

In addition, the guide portion 30 has a geometric structure wherein the guide portion 30 protrudes from the tip portion 10 to protect the tip portion 10 from damage due to force applied in a horizontal direction, whereby stability in a vertical direction is secured. As illustrated in FIGS. 1 and 2, the guide portion 30 may be realized in various embodiments such as an embodiment wherein the guide protrusion 32 protrudes from one side among four sides of the support member 31 corresponding to the tip portion 10 having a quadrangular pyramidal shape, and an embodiment wherein the guide protrusions 32 protrude from two to four sides of the support member 31.

Figure 3A:
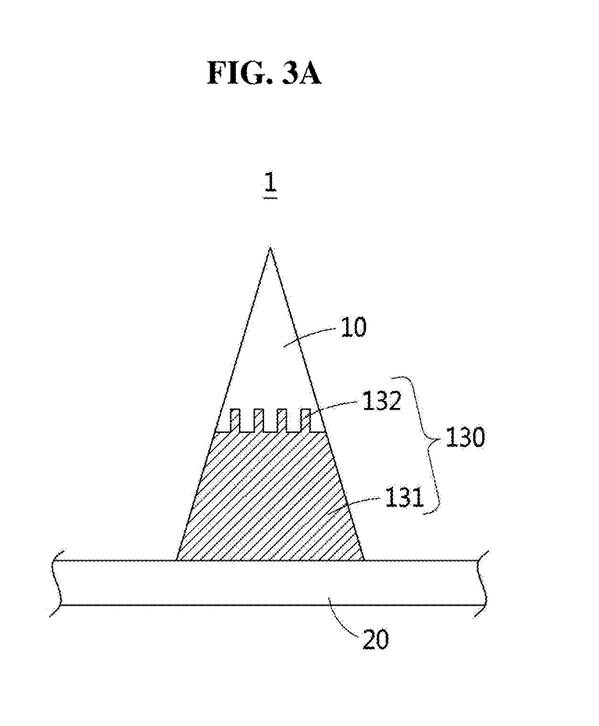
FIGS. 3A to 3D schematically illustrate side views of modified embodiments of the microneedle illustrated in FIG. 1.

For example, as illustrated in FIG. 3A, an upper surface of a support member 131 may be formed as a flat surface and a plurality of guide protrusions 132 may protrude from the upper surface of the support member 131. Here, the support member 131 of the guide portion 130 and the guide protrusions 132 are integrally formed with each other.

Figure 3B:
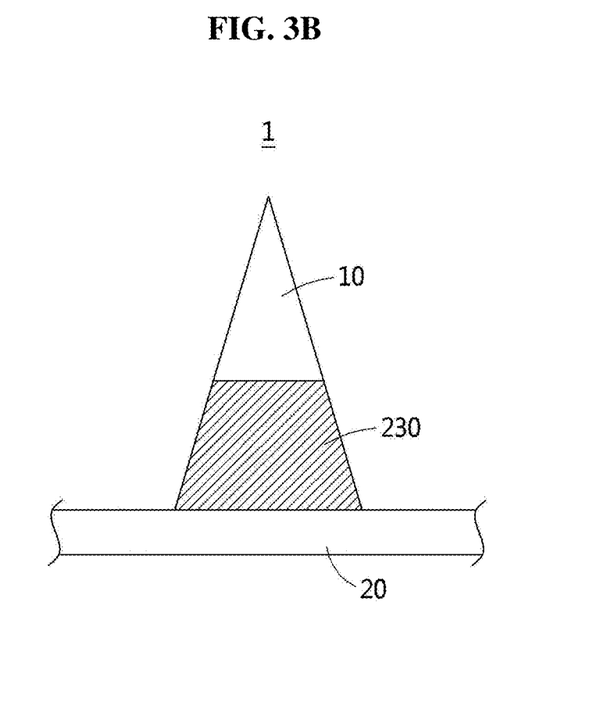

In a modified embodiment of FIG. 3B, a guide portion 230 is formed as one body. That is, the guide portion 230 is formed as one body without being separated into the support member 31 and the guide protrusion 32 as illustrated in FIGS. 1 and 2. In this case, as illustrated in FIG. 3B, the guide portion 230 protrudes from the base portion 20 in a penetration direction and the tip portion 10 is coupled with an upper surface of the guide portion 230.

Figure 3C:
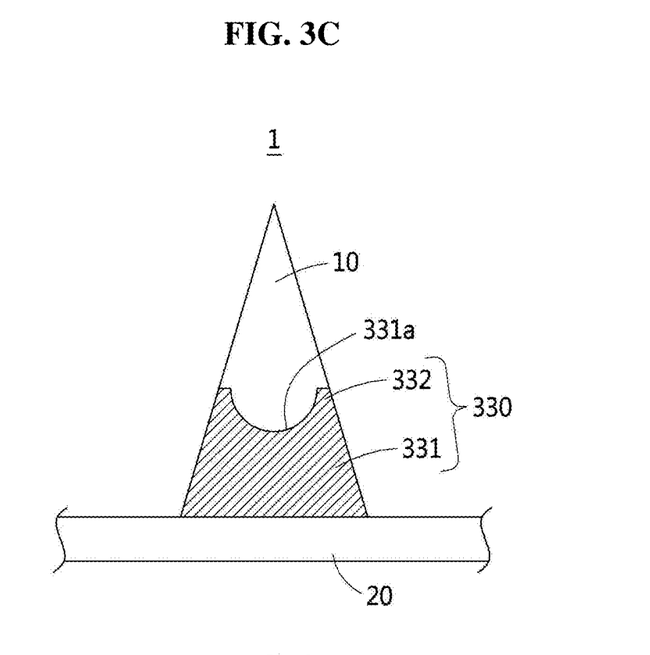

In the case of a modified embodiment illustrated in FIG. 3C, a concave semicircular support groove 331a is formed on an upper surface of a support member 331 of a guide portion 330, and at least one guide protrusion 332 extends from a rim of the concave semicircular support groove 331a. Here, the at least one guide protrusion 332 protrudes along the rim of the concave semicircular support groove 331a, thereby having a cross section wherein a hollow space is formed therein.

Figure 3D:
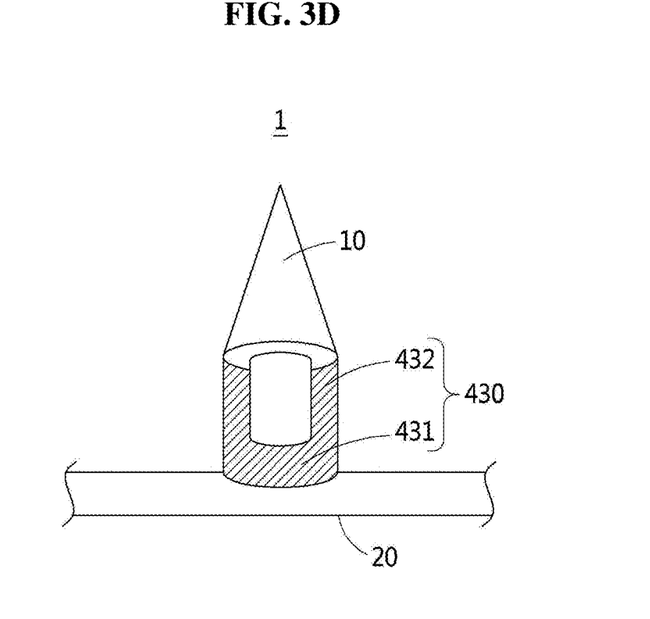

In the case of a modified embodiment illustrated in FIG. 3D, a support member 431 of a guide portion 430 extends from a base portion 20 in a cylindrical shape and a guide protrusion 432 protrudes along a rim of the support member 431. Here, since the guide protrusion 432 circumferentially protrudes along a rim of the support member 431, the guide protrusion 432 has a donut-shape cross section, an inside of which is empty.

As described above, each of the guide portions 30 (130, 230, 330, or 430) penetrates the skin (S) while supporting, in a penetration direction, at least a portion of the tip portion 10 along the shape of the tip portion 10. The guide portion 30 may have a total length of about 10 to 800 μm, a volume of 0.1 μm$^3$ to 1 mm$^3$, and an angle of 10 to 90. In addition, the shape of the guide portion 30 may be modified in various shapes such as a square, a trapezoid, an ellipse, a cross, and a shell.

Figure 4A:
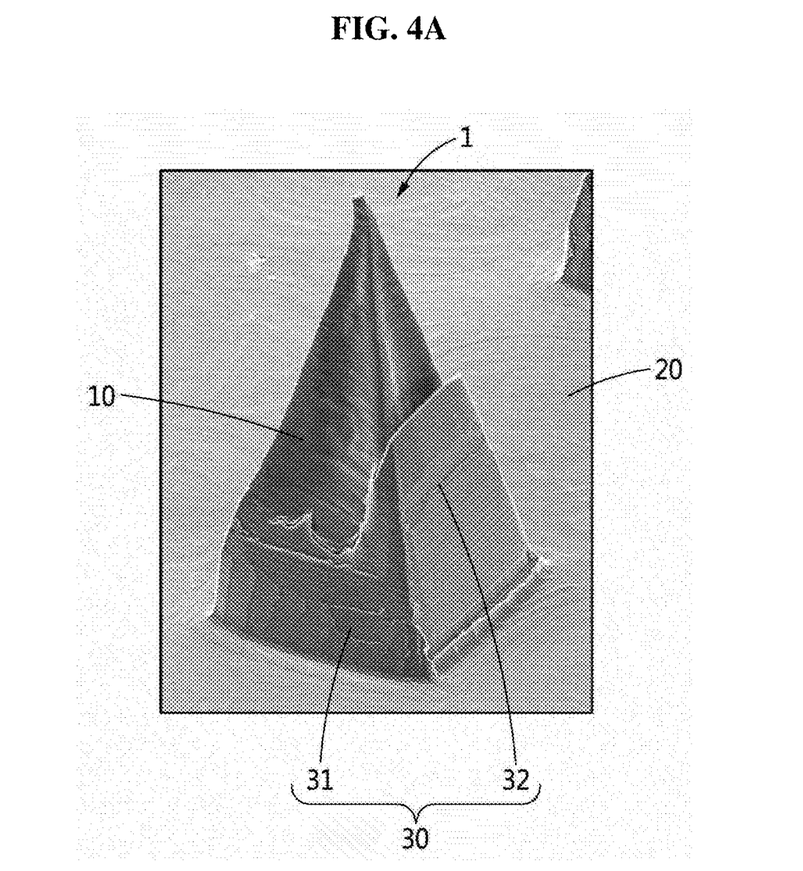
FIG. 4A schematically illustrates an image obtained by observing the microneedle illustrated in FIG. 1 with an optical microscope.
Figure 4B:
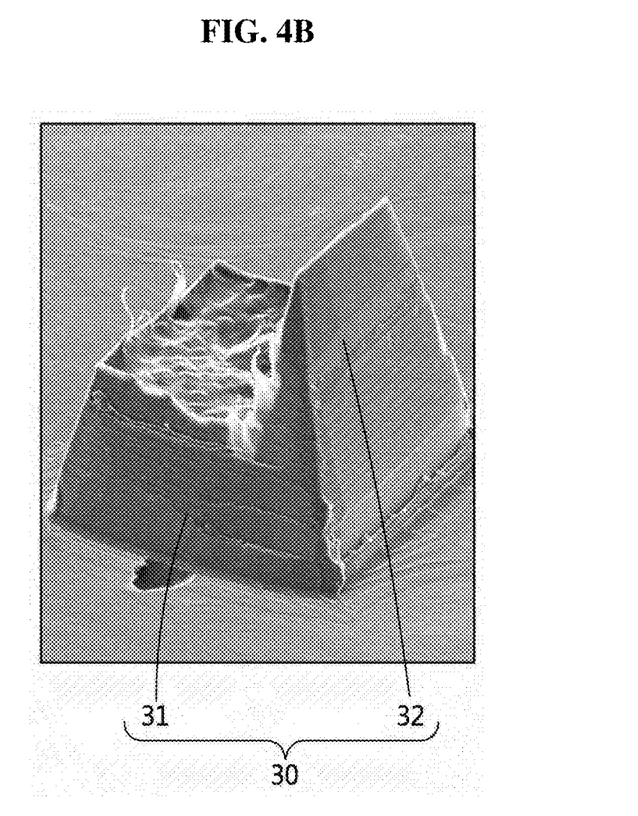
FIG. 4B schematically illustrates an optical microscope image obtained by penetrating the microneedle illustrated in FIG. 4A into the skin so that a tip portion thereof is separated.
Figure 5:
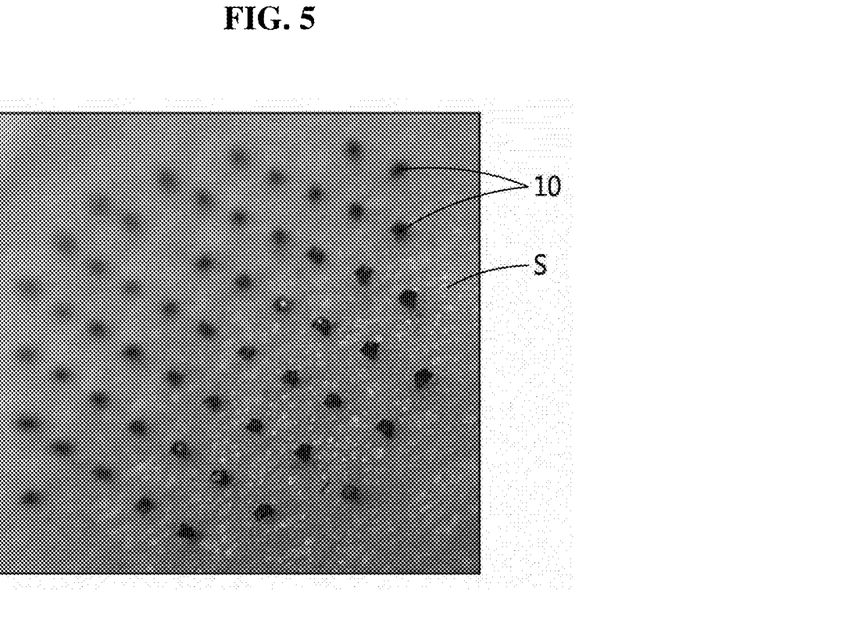
FIG. 5 is an optical microscope image schematically illustrating a state that a tip portion of the microneedle illustrated in FIG. 1 is separated and penetrates the skin.

An optical microscope image of the microneedle 1 having the aforementioned configuration according to the present disclosure is illustrated in FIGS. 4A and 4B. As illustrated in FIG. 4A, the microneedle 1 has a structure wherein the guide portion 30 is located between the tip portion 10 and the base portion 20. As illustrated in FIG. 4B, when the microneedle 1 penetrates the skin (S), the tip portion 10 alone is separated. Accordingly, as illustrated in FIG. 5, a predetermined amount of medicine may be supplied due to the tip portion 10 having penetrated the skin (S).

Figure 6:
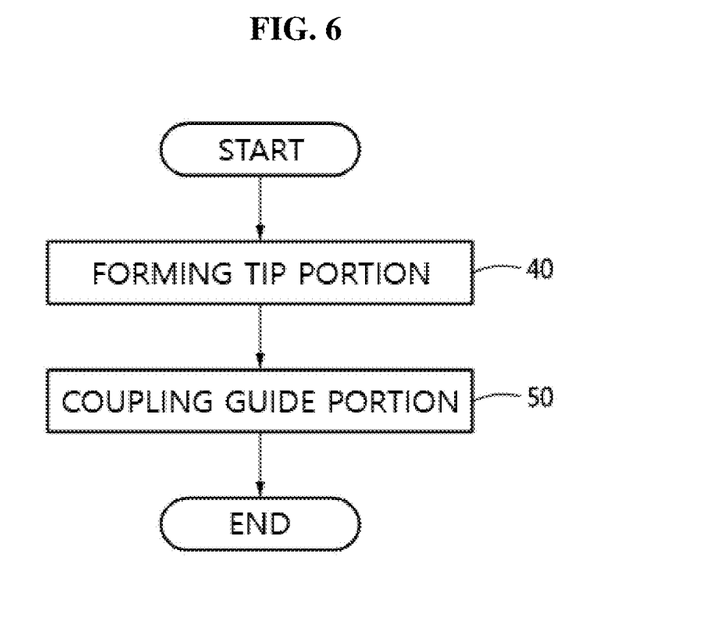
FIG. 6 is a flowchart schematically illustrating a procedure of a method of manufacturing a microneedle according to a preferred embodiment of the present disclosure.

Referring to FIG. 6, a method of manufacturing the microneedle 1 includes a step (40) of forming the tip portions 10 and a step (50) of coupling the guide portions 30.

Figure 7:
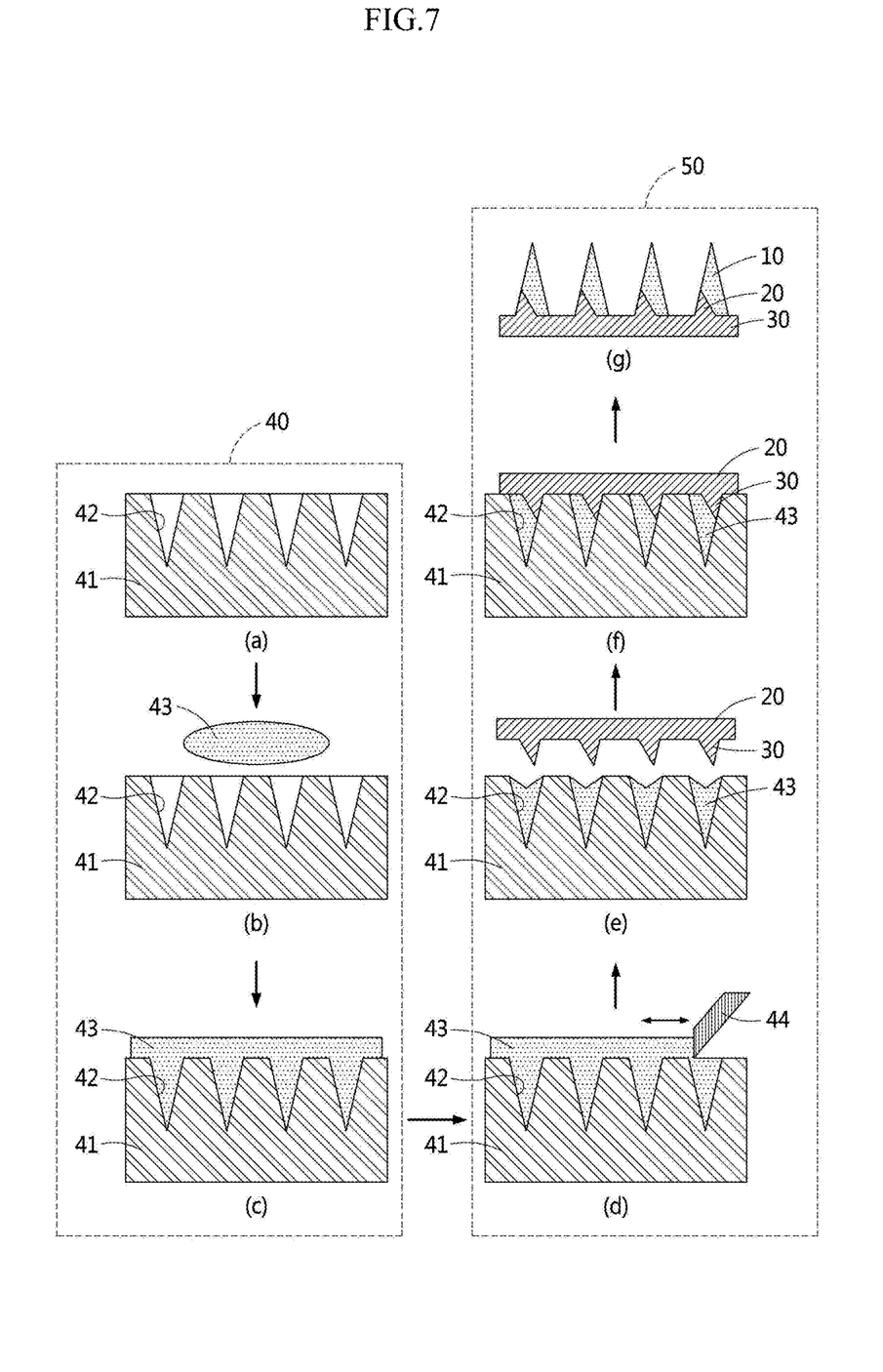
FIG. 7 illustrates microneedle manufacturing steps according to the method of FIG. 6.

In step (40) of forming the tip portions 10, the tip portions 10 including a liquid medicine capable of penetrating the skin (S) and being melted therein are formed. As illustrated in FIG. 7, the step (40) of forming the tip portions 10 includes a step of preparing a mold 41 having a plurality of tip grooves 42 (see FIG. 7(a)), a step of supplying a liquid medicine 43 including at least a portion of a raw material or biodegradable polymer ingredient into the mold 41 (see FIG. 7(b)), and a step of pressing the liquid medicine 43 into the tip grooves 42 to mold the tip portions 10 (see FIG. 7(c)).

Here, the tip grooves 42 have a cone or polygonal cone shape corresponding the shape of the tip portion 10 to be formed, and prepared by cutting the mold 41 inward. In addition, the mold 41 is a polydimethylsiloxane (PDMS) mold and includes a structure including at least any one of polyurethane, a metal, a biocompatible aluminum material, a water-soluble polymer, a lipophilic polymer, and an amphiphilic polymer.

The lipophilic polymer and the amphiphilic polymer are exemplified as including at least any one of hydroxypropyl cellulose (HPC), hydroxypropyl methyl cellulose (HPMC), polycaprolactone (PCL), polyglycolide (PGA), polylactic acid (PLA), a polylactide-glycolide (PLGA) copolymer, polyvinylpyrrolidone (PVP), polyethylene glycol (PEG), polyethylene oxide (PEO), polypropylene oxide (PPO), poly (vinyl methyl ether) (PVME), poly(methyl acrylate) (PMA), propylene glycol, polyesteramide, polybutyric acid, acrylamide (acrylic amide), acrylic acid, hyaluronic acid (HA), and gelatin.

In addition, the liquid medicine 43 injected into the tip grooves 42 of the mold 41 is formed of a biocompatible material and an additive. Here, the biocompatible material includes at least any one of carboxymethyl cellulose (CMC), hyaluronic acid (HA), alginic acid, pectin, carrageenan, chondroitin sulfate, dextran sulfate, chitosan, polylysine, carboxymethyl chitin, fibrin, agarose, pullulan, polyanhydride, polyorthoester, polyetherester, polyesteramide, polybutyric acid, poly(valeric acid), polyacrylate, an ethylene-vinyl acetate polymer, acryl-substituted cellulose acetate, polyvinyl chloride, polyvinyl fluoride, polyvinyl imidazole, chlorosulphonate polyolefins, polyethylene oxide, polyvinylpyrrolidone (PVP), hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or at least one of a copolymer of monomers forming this polymer and cellulose.

In addition, the additive included in the liquid medicine 43 includes at least any one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, gentiobiose, cetrimide (alkyltrimethylammonium bromide), cetrimonium bromide (hexadecyltrimethylammonium bromide (CTAB)), benzethonium chloride, docusate sodium salt, a SPAN-type surfactant, polysorbate (Tween)), sodium lauryl sulfate (sodium dodecyl sulfate (SDS)), benzalkonium chloride, and glyceryl oleate.

In step (50) of coupling the guide portions 30, the guide portions 30 are coupled with the tip portions 10 to respectively correspond to the tip portions 10. Here, after the step (40) of forming the tip portions 10, the tip portions 10 formed in the tip grooves 42 are present in a dried state.

For reference, since the tip portions 10 may be dried when the tip portions 10 are only formed regardless of the base portion 20 and the guide portions 30, a process time may be reduced by 70% or more, compared to a conventional manner wherein the tip portions 10 are dried along with the base portion 20.

In the step (50) of coupling the guide portions 30, the liquid medicine 43 molded outside the tip grooves 42 of the mold 41 is first removed as illustrated in FIG. 7(*d*). Here, the liquid medicine 43 outside the tip grooves 42 is removed with a predetermined removal means such as a cutter 44.

After the liquid medicine 43 outside the tip grooves 42 is removed, the guide portions 30 are coupled with the tip portions 10 molded into the tip grooves 42 as illustrated in FIGS. 7(*e*) and 7(*f*). Here, the guide portions 30 are integrally manufactured with the base portion 20, thereby being advantageous in coupling with the tip portion 10. That is, in a state in which the base portion 20 supports the guide portions 30 corresponding to the tip portions 10, the guide portions 30 are coupled with the tip portion 10 molded into the tip grooves 42.

Here, the base portion 20 is preferably formed of at least any one selected from the group consisting of polyethylene (PE), polypropylene (PP), polytetrafluoroethylene (PTFE), polymethyl methacrylate (PMMA), ethylene vinyl acetate (EVA), polycaprolactone (PCL), polyurethane (PU), polyethylene terephthalate (PET), polyethylene glycol (PEG), polyvinyl alcohol (PVA), polylactide (PLA), a polylactide-glycolide (PLGA) copolymer, and polyglycolide (PGA). In addition, the guide portions 30 and the base portion 20 are preferably formed of the same material. Since the base portion 20 and the guide portions 30 are not dissolved due to characteristics of a material thereof, loss due to dispersion of the liquid medicine 43 may be prevented.

When the tip grooves 42 and the guide portions 30 are coupled with each other, the mold 41 is removed as illustrated in FIG. 7(*g*), whereby the microneedle 1 is manufactured.

Meanwhile, although not illustrated, after coupling the tip portions 10 with the guide portions 30 to manufacture the microneedle 1, the microneedle 1 may be rapidly cooled and then surface-coated with a coating agent. In this case, in the rapid cooling, a refrigerant for inducing endothermic reaction including at least any one of liquid nitrogen at −196° C., tetrafluoroethane at −50° C., a Peltier element cooling fan −20° C., dry ice at −78° C., and a refrigerant including at least any one of carbon tetrachloride, trichlorofluoromethane, dichlorodifluoromethane, bromochlorodifluoromethane, dibromodifluoromethane, chlorotrifluoromethane, bromotrifluoromethane, tetrafluoromethane, chloroform, dichlorofluoromethane, chlorodifluoromethane, bromodifluoromethane, trifluoromethane, dichloromethane, chlorofluoromethane, methylene fluoride (difluoromethane), methyl chloride (chloromethane), methyl fluoride (fluoromethane), methane, hexachloroethane, pentachlorofluoroethane, tetrachlorodifluoroethane, trichlorotrifluoroethane, dichlorotetrafluoroethane (1,2-dichlorotetrafluoroethane), dibromotetrafluoroethane, chloropentafluoroethane, hexafluoroethane, pentachloroethane, dichlorotrifluoroethane (2,2-dichloro-1,1,1-trifluoroethane), chlorotetrafluoroethane, pentafluoroethane, tetratrifluoroethane, tetrafluoroethane, trichloroethane (methyl chloroform), dichlorofluoroethane (1,1-dichloro-1-fluoroethane), chlorodifluoroethane, trifluoroethane, dichloroethane, difluoroethane, ethyl chloride (chloroethane), ethane, dichlorohexafluoropropane, liquid helium, and liquid oxygen may be used.

In addition, in the coating step, a coating agent including the liquid medicine may be sprayed to the tip portions 10 or the tip portion 10 may be immersed in a coating agent to coat the tip portion 10. The coating step is preferably performed under vacuum or in a dry air environment having humidity of less than 50%. Here, the coating agent is mixed in a ratio of 0.1% to 90% of an effective ingredient, more preferably in a ratio of 0.1% to 30% of an effective ingredient, with water.

Meanwhile, the coating agent includes a thickener. The thickener includes at least any one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly(butyric acid), poly(valeric acid), polyacrylate, an ethylene-vinyl acetate polymer, acryl-substituted cellulose acetate, polyvinyl chloride, polyvinyl fluoride, poly (vinyl imidazole), chlorosulphonate polyolefins, polyethylene oxide, polyvinylpyrrolidone (PVP), hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or at least any one of a copolymer of monomers forming this polymer and cellulose.

The effective ingredient may include at least any one of α-interferon, β-interferon for multiple sclerosis, erythropoietin, follitropin β, follitropin α, G-CSF, GM-CSF, human chorionic gonadotropin, luteinizing hormone, salmon calcitonin, glucagon, a GNRH antagonist, insulin, human growth hormone, filgrastim, heparin, low-molecular-weight heparin, and somatotropin. Alternatively, the effective ingredient may include a vaccine including at least any one of Japanese encephalitis vaccine, rotavirus vaccine, influenza vaccine, polio vaccine, varicella vaccine, Alzheimer's disease vaccine, arteriosclerosis vaccine, cancer vaccine, nicotine vaccine, diphtheria vaccine, cervical cancer vaccine, meningococcal vaccine, tetanus vaccine, pertussis vaccine, Lyme disease vaccine, rabies vaccine, pneumococcal vaccine, yellow fever vaccine, cholera vaccine, vaccine exanthem, tuberculosis vaccine, rubella vaccine, measles vaccine, mumps vaccine, botulism vaccine, herpes virus vaccine, other DNA vaccines, hepatitis B vaccine, hyaluronic acid, Coenzyme Q10, chitosan, Botox, vitamins and vitamin derivatives, hydroxy acid, tetracycline, oxytetracycline, doxycycline, minocycline, benzocaine, mepivacaine, lidocaine, prilocaine, bupivacaine, etidocaine, articaine, procaine, propoxycaine, tetracaine, ropivacaine, butacaine, piperocaine, cocaine, chloroprocaine, proparacaine, and dyclonine.

Meanwhile, the coating agent includes a water-soluble substance. The water-soluble substance includes at least any one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

In addition, a solvent is evaporated from the coated microneedle 1. The microneedle 1 is preferably waterproof-coated such that the coated surface thereof is not affected by a solution. Here, the waterproof coating may be performed in an manner in which a solvent is evaporated from the coated tip portion 10 by at least any one of ultrasonic spray coating, atomization coating, electro-spinning coating, or dip coating.

In addition, in the waterproof coating, an end or the entire surface of the microneedle 1 is preferably coated with a water-repellent agent including a mineral-based material or a lipid-based material. Here, the water-repellent agent includes at least any one of beeswax, oleic acid, soy fatty acid, castor oil, phosphatidylcholine, vitamin E (d-α-tocopherol/Vitamin E), corn oil mono-di-tridiglycerides, cottonseed oil, olive oil, peanut oil, peppermint oil, safflower oil, sesame oil, soybean oil, hydrogenated vegetable oils, hydrogenated soybean oil, capric triglycerides (caprylic/capric triglycerides derived from coconut oil or palm seed oil) and phosphatidylcholine, or is formed of a mixture thereof.

Since the microneedle 1 is manufactured by coupling the tip portions 10, as a water-soluble substance, with the base portion 20 and guide portions 30 formed of a non-soluble material as described above, a predetermined amount of liquid medicine in the tip portions 10 alone penetrates the skin (S) when the microneedle 1 penetrates the skin (S). In addition, since a coupling force between the guide portions 30 and the tip portion 10 is smaller than a force with which the skin (S) holds the tip portions 10, the tip portion 10 having penetrated the skin (S) is rapidly separated from the guide portions 30, whereby penetration force is increased. Further, since the guide portions 30 protrude in a penetration direction, the guide portions 30 may be instantly separated from the tip portions 10 in the skin (S) using user's finger force without a mechanical device such as a high-pressure applicator.

In accordance with the present disclosure having the aforementioned configuration, first, only a predetermined amount of liquid medicine forming the tip portion may penetrate the skin because the tip portion penetrates the skin in a state in which the tip portion is coupled with the guide portion that protrudes in a penetration direction and is formed of a non-soluble material, whereby loss of the liquid medicine may be reduced.

Second, since a force with which the skin holds the tip portion is larger than a coupling force between the tip portion and the guide portion, the tip portion having penetrated the skin may be instantly separated from the guide portion.

Third, treatment quality may be improved due to supply of a predetermined amount of liquid medicine and rapid penetration force.

Fourth, due to the guide portion and base portion formed of a non-soluble material, drying of which is unnecessary, manufacturing time may be effectively reduced and stability of an effective ingredient may be increased.

Fifth, due to the guide portion protruding in a penetration direction, a medicine may be instantly administered using user's finger force without a high-pressure applicator, thereby increasing convenience.

While the present invention has been described referring to the preferred embodiments of the present invention, those skilled in the art will appreciate that many modifications and changes can be made to the present invention without departing from the spirit and essential characteristics of the present invention.

DESCRIPTION OF SYMBOLS

| 1: MICRONEEDLE | 10: TIP PORTION |
|---|---|
| 20: BASE PORTION | 30: GUIDE PORTION |
| 31: SUPPORT MEMBER | 32: GUIDE PROTRUSION |
| S: SKIN | |

What is claimed is:

1. A microneedle comprising:
   a base portion,
   a guide portion extending from the base portion, and
   a water soluble tip portion coupled to the guide portion, wherein the tip portion is capable of penetrating a skin and comprises a medicine;
   wherein the base portion and the guide portion are not soluble in water,
   wherein the combination of the tip portion and the guide portion is in a quadrangular pyramidal shape,
   wherein the guide portion is composed of a support member and a guide protrusion such that the support member extends from the base portion and forms the bottom of the pyramid,
   wherein the guide protrusion extends from three of the four sides of the support member and the tip portion composes the remainder of the pyramid,
   wherein the sides of the guide protrusion that extend from opposite sides of the support member are each in a triangular shape and the side of the guide protrusion extending from the third side of the support member is in a trapezoidal shape,
   wherein the tip portion has a distal end in a pointed tip shape that also forms the distal end of the microneedle,
   wherein the guide portion does not form a portion of the tip of the microneedle, and
   wherein the guide portion is coupled to the tip portion with a coupling force smaller than a force with which the skin holds the tip portion, and thus, when the guide portion causes the tip portion to penetrate the skin in the vertical direction and then is separated from the tip portion, the tip portion separated from the guide portion remains in the skin.

2. The microneedle according to claim 1, wherein the guide portion is integrally formed with the base portion.

3. The microneedle according to claim 1, wherein the support member and the guide protrusion are formed as one body.

* * * * *